United States Patent [19]
Burbank et al.

[11] Patent Number: 6,007,516
[45] Date of Patent: *Dec. 28, 1999

[54] VALVE PORT AND METHOD FOR VASCULAR ACCESS

[75] Inventors: Jeffrey H. Burbank, Boxford, Mass.; C. David Finch, Clinton, Miss.; James M. Brugger, Newburyport, Mass.; Hendrik E. Kuiper, Edwards, Miss.

[73] Assignee: Vasca, Inc., Tewksbury, Mass.

[*] Notice: This patent issued on a continued prosecution application filed under 37 CFR 1.53(d), and is subject to the twenty year patent term provisions of 35 U.S.C. 154(a)(2).

[21] Appl. No.: 08/942,990

[22] Filed: Oct. 2, 1997

Related U.S. Application Data

[60] Provisional application No. 60/036,124, Jan. 21, 1997.

[51] Int. Cl.⁶ .................................................. A61M 11/00
[52] U.S. Cl. ........................... 604/93; 604/245; 604/256; 251/7; 251/149.7
[58] Field of Search .................. 604/4, 49, 53, 604/93, 167, 175, 264, 246, 245, 249, 250, 256, 891.1; 251/149.6, 149.7, 7

[56] References Cited

U.S. PATENT DOCUMENTS

| | | |
|---|---|---|
| 3,998,222 | 12/1976 | Shihata . |
| 4,181,132 | 1/1980 | Parks . |
| 4,534,759 | 8/1985 | Trawöger . |
| 4,557,722 | 12/1985 | Harris ........................... 604/9 |
| 4,569,675 | 2/1986 | Prosl et al. . |
| 5,045,060 | 9/1991 | Melsky et al. ................. 604/93 |
| 5,053,013 | 10/1991 | Ensminger et al. . |
| 5,057,084 | 10/1991 | Ensminger et al. . |
| 5,167,638 | 12/1992 | Felix et al. . |
| 5,180,365 | 1/1993 | Ensminger et al. . |
| 5,226,879 | 7/1993 | Ensminger et al. . |
| 5,263,930 | 11/1993 | Ensminger . |
| 5,281,199 | 1/1994 | Ensminger et al. . |
| 5,350,360 | 9/1994 | Ensminger et al. . |
| 5,356,381 | 10/1994 | Ensminger et al. . |
| 5,417,656 | 5/1995 | Ensminger et al. ............. 604/93 |
| 5,476,451 | 12/1995 | Ensminger et al. . |
| 5,476,460 | 12/1995 | Montalvo ..................... 604/891.1 |
| 5,503,630 | 4/1996 | Ensminger et al. . |
| 5,520,643 | 5/1996 | Ensminger et al. . |
| 5,527,277 | 6/1996 | Ensminger et al. . |
| 5,527,278 | 6/1996 | Ensminger et al. . |
| 5,562,617 | 10/1996 | Finch, Jr. et al. . |
| 5,637,088 | 6/1997 | Wenner et al. . |
| 5,702,363 | 12/1997 | Flaherty . |
| 5,741,228 | 4/1998 | Lambrecht et al. .............. 604/93 |
| 5,755,780 | 5/1998 | Finch, Jr. et al. ............... 623/1 |
| 5,762,805 | 6/1998 | Truitt et al. ................... 210/645 |

FOREIGN PATENT DOCUMENTS

| | | |
|---|---|---|
| 0110117 | 6/1984 | European Pat. Off. . |
| 0159260 | 10/1985 | European Pat. Off. . |
| 196 03 178 | 1/1996 | Germany . |
| WO 83/02063 | 6/1983 | WIPO . |
| WO 93/00129 | 6/1992 | WIPO . |
| WO 94/05246 | 9/1993 | WIPO . |
| WO 94/05246 | 3/1994 | WIPO . |
| WO 94/05351 | 3/1994 | WIPO . |
| WO 95/19200 | 7/1995 | WIPO ..................... A61M 39/02 |
| WO 96/25196 | 8/1996 | WIPO . |
| WO 96/31246 | 10/1996 | WIPO ..................... A61M 5/142 |
| WO 97/47338 | 12/1997 | WIPO ..................... A61M 5/00 |

OTHER PUBLICATIONS

English translation of German Patent Publication No. DE 19603178 (filed Jan. 30, 1996) 16 pages total.

*Primary Examiner*—Wynn Wood Coggins
*Assistant Examiner*—LoAn H. Thanh
*Attorney, Agent, or Firm*—Townsend and Townsend and Crew LLP

[57] ABSTRACT

An access port comprises a base and a flexible conduit. The port is subcutaneously implanted and the conduit is attached directly or indirectly to a blood vessel or other body lumen or cavity. An actuator mechanism is provided with a linkage which opens a valve in the port in response to percutaneous insertion of a needle into the access port. In particular, insertion of the needle opens the clamping mechanism to permit flow through the conduit between the blood vessel and the needle.

124 Claims, 9 Drawing Sheets

VALVE PORT AND METHOD FOR VASCULAR ACCESS

The present application is a continuation-in-part of provisional Application Ser. No. 60/036,124, filed on Jan. 21, 1997, the full disclosure of which is incorporated herein by reference.

BACKGROUND OF THE INVENTION

1. Field of the Invention

The present invention relates generally to the design and use of medical devices, and more particularly to the design and use of an implantable port for establishing temporary access to a patient's vascular system for hemodialysis and other extracorporeal blood treatments. Access to a patient's vascular system can be established by a variety of temporary and permanently implanted devices. Most simply, temporary access can be provided by the direct percutaneous introduction of a needle through the patient's skin and into a blood vessel. While such a direct approach is relatively simple and suitable for applications, such as intravenous feeding, intravenous drug delivery, and other applications which are limited in time, they are not suitable for hemodialysis and other extracorporeal procedures that must be repeated periodically, often for the lifetime of the patient.

For hemodialysis and other extracorporeal treatment regimens, a variety of implantable ports have been proposed over the years. Typically, the port includes a chamber on an access region, such as a septum, and the chamber is attached to an implanted catheter which in turn is secured to a blood vessel. In the case of veins, the catheter is typically indwelling and in the case of arteries, the catheter may be attached by conventional anastomosis.

Of particular interest to the present invention, implantable ports typically include a needle-penetrable septum which permits the percutaneous penetration of a needle into the internal chamber. The chamber, in turn, is connected to one end of the catheter, and the other end of the catheter is indwelling in the blood vessel. While workable, such designs suffer from a number of problems. Repeated penetration of the septum often leads to degradation over time, presenting a substantial risk of small particulates entering the blood stream and/or need to periodically replace the port. Second, the passage of blood through the chamber or plenum will often encounter regions of turbulence or low flow, either of which can degrade the quality of blood over time. Third, many previous vascular access ports have failed to provide an internal valve structure which isolates the interior of the port from the lumen of the implanted catheter when the port is not in use. Fourth, in previous ports which employ a valve, self-penetrating needles are not used since they will be damaged by and/or cause damage to the port. In such instances, it is frequently necessary to use a catheter combined with a removable stylet, which is both more costly and more inconvenient than use of a simple needle. Fifth, in ports which employ either septums or valves, the needle or other access device is prone to accidental dislodgement. Loss of a needle from a blood return port is particularly dangerous since blood may continue to be withdrawn while it is simultaneously being lost to the environment. While needle and port designs have been proposed for preventing such accidental dislodgement, most such designs are complex and are not themselves fail safe.

A number of vascular access designs have been proposed which address at least some of the problems. In particular, a series of issued U.S. Patents which name William Ensminger as an inventor disclose access ports having internal lumens for receiving a percutaneously introduced access device (e.g. a needle or catheter/stylet combination) and internal valve structures for isolating the port from an associated implanted catheter. These patents, which are listed herein below, disclose a number of specific valve types which may be incorporated within the access port, including leaflet valves, ball valves, flapper valves, and other specific configurations which are referred to as "articulating valves." All such structures, however, generally require that the access device be passed through the valve itself (i.e., the portion which closes the blood flow path through the valve) in order to cause the valve to open. Such a requirement presents the risk that the valve will be degraded by direct contact with the access device after repeated uses so that portions of the valve may be degraded and released into circulation. Such valves also present a significant risk of failure after repeated use or contact with a sharpened needle. Additionally, such valve structures can damage the access device as it is being introduced therethrough, thus potentially disrupting valve flow through the needle during a subsequent treatment protocol.

An additional problem with the valves of Ensminger is that the entry ports are usually inclined at a substantial angle relative to the skin surface through which the access device is introduced. Such angled access requires that the personnel introducing the access device guess the angle and estimate the optimum insertion point on the patient's skin. Such uncertainty in the device penetration is perhaps why the Ensminger designs all require the use of enlarged "funnel" for receiving and aligning the needle as it is introduced. It would thus be advantageous to provide access ports having entry passages which are disposed generally "vertically" (i.e., at an angle which is substantially normal to the skin surface through which the needle is being introduced). By penetrating the needle "straight in," it is much easier to align the needle with the target orifice and the size of the orifice (needle penetration) area can be reduced.

For these reasons, it would be desirable to provide improved implantable access ports for percutaneously accessing a patient's blood vessels, including both arteries and veins. The access ports preferably will comprise a valve structure for isolating the port from an associated implanted catheter when the port is not in use. The valve will preferably provide little or no structure within the blood flow lumen of the access port and will even more preferably not require passage of a needle or other access tube through the seating portion of a valve in order to open the valve. Furthermore, the port structure including the valve elements therein will have a substantially uniform cross-sectional area and will present no significant constrictions or enlargements to disturb fluid flow therethrough. Preferably, the port designs will permit percutaneous access using a conventional needle, such as a fistula needle, without damage to either the port or the needle. Still more preferably, the needles or other devices used to access the port will resist accidental dislodgement from the port without requiring significant extra structure or additional components. Ports and valves according to the present invention will meet at least some of these objectives.

2. Description of the Background Art

U.S. Pat. No. 5,562,617 and WO 95/19200, assigned to the assignee of the present application, describe implantable vascular access systems comprising an access port having an internal slit or duck bill valve for preventing back flow into the port. Vascular access ports having various articulating valves for isolating the port from the vascular system in the absence of external percutaneous connection to the port are described in the following U.S. Patents which name William Ensminger as an inventor: U.S. Pat. Nos. 5,527,278; 5,527,277; 5,520,643; 5,503,630; 5,476,451; 5,417,656; 5,350,360; 5,281,199; 5,263,930; 5,226,879; 5,180,365; 5,057,084; and 5,053,013. Other patents and published applications which show implantable ports having valve structures opened by insertion of a needle include U.S. Pat. Nos. 4,569,675; 4,534,759; 4,181,132; 3,998,222; and WO 96/31246. U.S. Pat. No. 5,637,088 describes a septum-type implantable port which employs a dual needle to help prevent dislodgement.

SUMMARY OF THE INVENTION

The present invention provides improved access ports, particularly vascular access ports which may be used for high volume withdrawal and/or return of blood or other fluids particularly for patients undergoing an extracorporeal blood therapy, such as hemodialysis, hemofiltration, hemodiafiltration, apheresis, or the like. The vascular access ports allow for high volumetric rates of blood or other fluid flow therethrough, typically allowing for rates above 250 ml/min, usually above 300 ml/min, preferably at least 400 ml/min, and often 500 ml/min or higher, using a single needle or other access device. Such high volumetric flow rates are quite advantageous in reducing the time required for performing the extracorporeal blood treatment, particularly for otherwise lengthy treatments which require large total volumes of treated blood, such as hemofiltration. Although the access ports are particularly useful for establishing vascular access, the ports will also be useful for accessing other body lumens and cavities, such as the peritoneal cavity, and the like.

In addition to their high capacity, the access ports of the present invention have a number of other advantageous features. In particular, the access ports are adapted to receive standard sharp access needles, including large-diameter fistula needles, without substantial damage to either the port or the needle. The port design also provides for simple "locking" and "unlocking" of the needle or access device as it is inserted and removed from the port, as described in more detail below. These and other design aspects of the access ports will be explained more fully in connection with the detailed description below.

According to a first aspect of the method of the present invention, percutaneous access to a blood vessel is provided by maintaining a conduit between an implanted access port and the blood vessel. When not connected to an extracorporeal treatment circuit, the access port is isolated from the blood vessel by externally clamping the conduit, which is typically formed at least partly from a resilient material, such as silicone rubber. Percutaneous insertion of an access tube into the access port relieves the external clamping of the conduit in order to permit fluid flow therethrough. Use of external clamping for isolating the access port is particularly advantageous since no internal valve structure is required to define a valve seat within the flow lumen.

Typically, a proximal end of the conduit is disposed within the access port while a distal end of the conduit is disposed outside of the access port, usually being attached to the blood vessel or other body lumen or being connected to an implanted catheter or other conduit which, in turn, is attached to the blood vessel. The conduit will usually comprise a single continuous tube, but could alternatively comprise a number of separate axial portions having different compositional or structural characteristics which are joined together, e.g. at a port on the housing. For example, a portion of the length of the conduit could be composed of a relatively rigid material, such as a hard plastic or metal, while only that portion which is subjected to external clamping need be composed of a flexible material which can be sealed by clamping. Additionally, the conduits could be bifurcated for connection to more than one body lumen site. In an alternative embodiment, the conduit is disposed entirely within the access port and a connection is provided on the access port for attachment to a separate catheter which may in turn be connected to the blood vessel.

Once implanted and connected to a blood vessel, the access port may be employed to receive blood flow from a blood vessel or provide other fluid flows, e.g. dialysate for peritoneal dialysis, typically an artery. Usually in such cases, a second access port is provided for connection to a vein for a return of blood to the patient. Any of the extracorporeal treatment modalities described above could be employed with the blood flow between the arterial access port and the venous access port. In yet another alternative, the access ports of the present invention could be used singly infusing fluids, drugs, and other substances to the patient.

In a second aspect of the method of the present invention, the conduit is maintained between an implanted access port and a blood vessel of the patient. An access tube is percutaneously inserted into the access port so that the access tube engages a linkage which opens a valve structure within the port or the conduit. The valve structure is located remotely from that portion of the access port into which the access tube has been inserted and may be present in the conduit itself or in a separate pinch tube or assembly within the port. The linkage may be mechanical or hydraulic, usually being mechanically coupled to a spring-loaded clamp which constricts a flexible (collapsible) portion of the conduit when the linkage is not engaged by the access tube. Alternatively, a hydraulic linkage could be provided where a closing force on the tube is hydraulically relieved or a valve opened by insertion of the access tube.

In a third aspect of the method of the present invention, percutaneous access to a patient's blood vessel is provided by maintaining a conduit between an implanted access port and the blood vessel. An access tube is percutaneously inserted into a tube seat within the access port to establish a generally fluid tight seal therein. When inserted, the access tube actuates a linkage to open a valve structure to permit flow through the conduit. The valve structure will usually be internal to the port but, in some cases, could be located outside of the port itself. Preferably, the tube seat comprises a tapered bore within the access port which frictionally engages the outside access tube as the tube is inserted into the bore. More preferably, insertion of the access tube into the tube seat depresses the tube seat relative to a base of the access port in order to actuate the linkage which opens the conduit. The linkage may take a variety of forms, including clamp valves as described above. The linkage may also be in the form of a sliding valve assembly, where the access tube advances a valve component to align flow passages therethrough to open the flow path within the port.

The tube seat will remain locked in its depressed condition until the access tube is removed from the base. By forming the tube seat from (or lining the tube seat with) a hard material, preferably a material harder than the needle or other access device which is to be used, the likelihood of damage to the valve can be greatly reduced. Moreover, the tapered tube seat design is not prone to damaging needles when they are inserted into the port. Thus, the port of the present invention is particularly suited for use with self-penetrating, sharpened needles, such as fistula needles, unlike many ports of the prior art.

In a fourth aspect in the method of the present invention, percutaneous access to a patient's blood vessels is provided by maintaining a conduit between an implanted access port and a blood vessel. An access tube is percutaneously inserted into the access port in a generally vertical orientation, i.e., in a direction normal or perpendicular to the surface of the patient's skin through which the access tube is being introduced. The passage in the access port is connected to the conduit through an elbow at an angle of from 75° to 105°. The ability to vertically introduce the access tube greatly simplifies alignment of the access tube with the passage in the port.

Apparatus according to the present invention comprise implantable ports having a base with a passage for receiving an access tube, such as a needle, rigid catheter, cannula, or other conventional device for receiving or returning blood flow or other fluid. In one embodiment, the flexible conduit is disposed within the base to establish fluid flow with an access tube which has been inserted through the passage. A linkage is further provided which opens the flexible conduit, typically by relieving an external clamp from over the conduit, when an access tube is present in the passage. The linkage further closes the flexible conduit when the access tube is absent from the passage. In another embodiment, the linkage is part of or coupled to a valve assembly. For example, the valve assembly may be a sliding valve and the linkage comprise a slide within the valve. In all cases, the linkage will be actuated by insertion of the access tube and will open the conduit, valve, or other part of the flow path at a location remote from the access tube.

The conduit of the implantable port will usually have a proximal end disposed within the base and a distal end disposed outside the base. When disposed outside of the base, the distal end will typically be adapted for direct connection to a blood vessel, e.g., by including a cuff which may be connected to the blood vessel by an end-to-side anastomosis or a T-catheter which may be implanted within the lumen of the blood vessel. Alternatively, the conduit may terminate in a connector which is adapted for removable connection to one end of a separate implantable catheter which may be connected to the blood vessel. As a further alternative, the flexible conduit may have a proximal end disposed within a base and a distal end which terminates on a luer or other conventional connector disposed on an external surface of the base. In such cases, the access port may be connected to a separate, implantable catheter through the connector on the surface of the base.

In preferred aspects of the apparatus of the present invention, the passage in the base comprises a tapered bore which seals externally against a needle or other access tube as the tube is inserted into the bore. In one embodiment, a flexible conduit is connected to an end of the tapered bore, and typically deflected at approximately a right angle (i.e., between 75° and 105°) to direct the conduit externally of the base. In another embodiment, the tapered bore is formed in a slide of a sliding valve.

In a second aspect of the apparatus of the present invention, an implantable port comprises a base having a passage and a flexible conduit, generally as described above. A clamp is disposed externally on the flexible conduit, wherein the clamp is closed over the conduit but opens to permit fluid flow through the conduit when an access tube is inserted into the passage within the base. Conversely, the clamp closes over the conduit when the access tube is removed from the passage. Preferably, such an implantable port further comprises a linkage assembly including an actuator which responds to entry of the access tube into the passage and which opens the clamp in response to such passage. Likewise, the actuator will respond to removal of the access tube from the passage in the base and close the clamp in response to such removal.

In a further aspect of the apparatus of the present invention, an implantable port comprises a base and a conduit, generally as described above. The passage within the base is oriented along a generally vertical access, i.e., normal to the portion of the patient's skin through which the access tube is to be introduced, and the conduit is disposed along a generally horizontal access.

In a more particular aspect of the apparatus of the present invention, an implantable port comprises a base having a first passage for receiving access tube and a flexible conduit disposed through a second passage in the base. An actuator assembly is reciprocatably mounted in the base and includes a bore aligned with the first passage for receiving the access tube. The proximal end of the conduit is mechanically coupled to the bore in an actuator assembly, a spring urges the actuator assembly to a first position in the base wherein the flexible conduit is closed and is opened by insertion of the access tube into the first passage. Preferably, the actuator assembly comprises a lower lip and the second passage in the base comprises an upper lip, wherein the upper lip and lower lip are opposed on opposite sides of the flexible conduit so that the flexible spring closes the lips together to close the lumen within the conduit when an access tube is inserted into the tube-receiving bore in the actuator.

In a still further particular aspect of the present invention, an implantable port comprises a base having a passage for receiving an access tube. A valve assembly is disposed in the base and includes a bore which is aligned with the passage in the base and which also receives the access tube. A pair of balls, typically opposed stainless steel balls similar in small ball bearings, are disposed between the passage in the base and the bore in the valve. The balls are spring-biased to close or engage against the access device when it is inserted through the passage and port. In particular, the balls will lock the access tube in place by frictional engagement so that it is very difficult to accidentally dislodge the access tube without following a specific removal procedure. Surprisingly, even though the access tube is held firmly in place by the locking balls and resists even very strong efforts to pull the access tube directly from the implanted port, the access tube can be readily removed by simply twisting or turning it about its own longitudinal axis while gently pulling thereon. Thus, while the access tube is firmly locked in place so that the likelihood of accidental removal is minimized, it can still be easily removed without damage to either the access tube or the port, or significant discomfort to the patient by a simple twisting and pulling procedure.

In yet another aspect of the present invention, an implantable port includes a base, a passage in the base for receiving a needle or other access tube, and an internal valve which opens and closes in response to insertion of the access tube into the passage. The implantable port comprises a symmetric configuration where the passage is disposed at a central location in the top of the port. Preferably, the passage has an entry aperture with an area in the range from 3 mm$^2$ to 20 mm$^2$, more preferably from 5 mm$^2$ to 15 mm$^2$. Such a port configuration facilitates percutaneous introduction of a needle or other access tube into the port. The user can manually locate the periphery of the port base, usually using one hand. With the other hand, the user can then insert the access tube in a generally vertical orientation directly into the center of the port where the entry aperture is located. Thus, access to the port is much simpler than with non-symmetric port configurations, particularly those ports which require the needle to enter in a non-vertical orientation relative to the patient's skin.

Improved body lumen access systems according to the present invention comprise an implantable port and an access tube. By providing a port having a passage for receiving the access tube, where the passage is composed of a material which is harder than the port, wear on the passage of the port is greatly reduced, thus increasing the useful life of the port. This is particularly important where the port is to be directly accessed using a needle having a sharpened tip. In the preferred embodiments, the passage will be generally cylindrical and have a tapered portion which seals against the exterior of the needle or other access tube therein.

The present invention still further provides methods for accessing a body lumen comprising subcutaneously implanting a port and subcutaneously implanting a conduit. The port has an inlet adapted to receive an access tube with an outer diameter of at least 2 mm. The conduit is attached to an outlet of the port and has a lumen diameter of at least 2.5 mm. The method usually further comprises accessing the implanted port with an access tube having an outer diameter of at least 2 mm. Such methods permit flow rates of at least 250 ml/min to be established when a differential pressure between the body lumen and an outlet end of the access tube of at least 200 mmHg exists. Usually, higher flow rates as set forth above can also be achieved. Preferably, the body lumen is a blood vessel and the fluid is blood, although the method is also useful for accessing other body lumens, e.g. the peritoneum or peritoneal dialysis.

In yet another aspect, the present invention provides an implantable port comprising a base having an inlet passage adapted to receive an access tube with an outer diameter of at least 2 mm and an outlet passage. A valve is disposed in the base between the inlet passage and the outlet passage, and the valve is adapted to open in response to insertion of the access tube into the inlet passage. A means is provided for attaching an implantable conduit having a lumen diameter of at least 2.5 mm to the outlet passage of the base, e.g. a connector on the base or a conduit extending from the base and having a connector at its distal end. The implantable port is particularly useful in the method just described. The system may further comprise an implantable conduit having a lumen diameter of at least 2.5 mm.

DESCRIPTION OF THE SPECIFIC EMBODIMENTS

Figure 1:
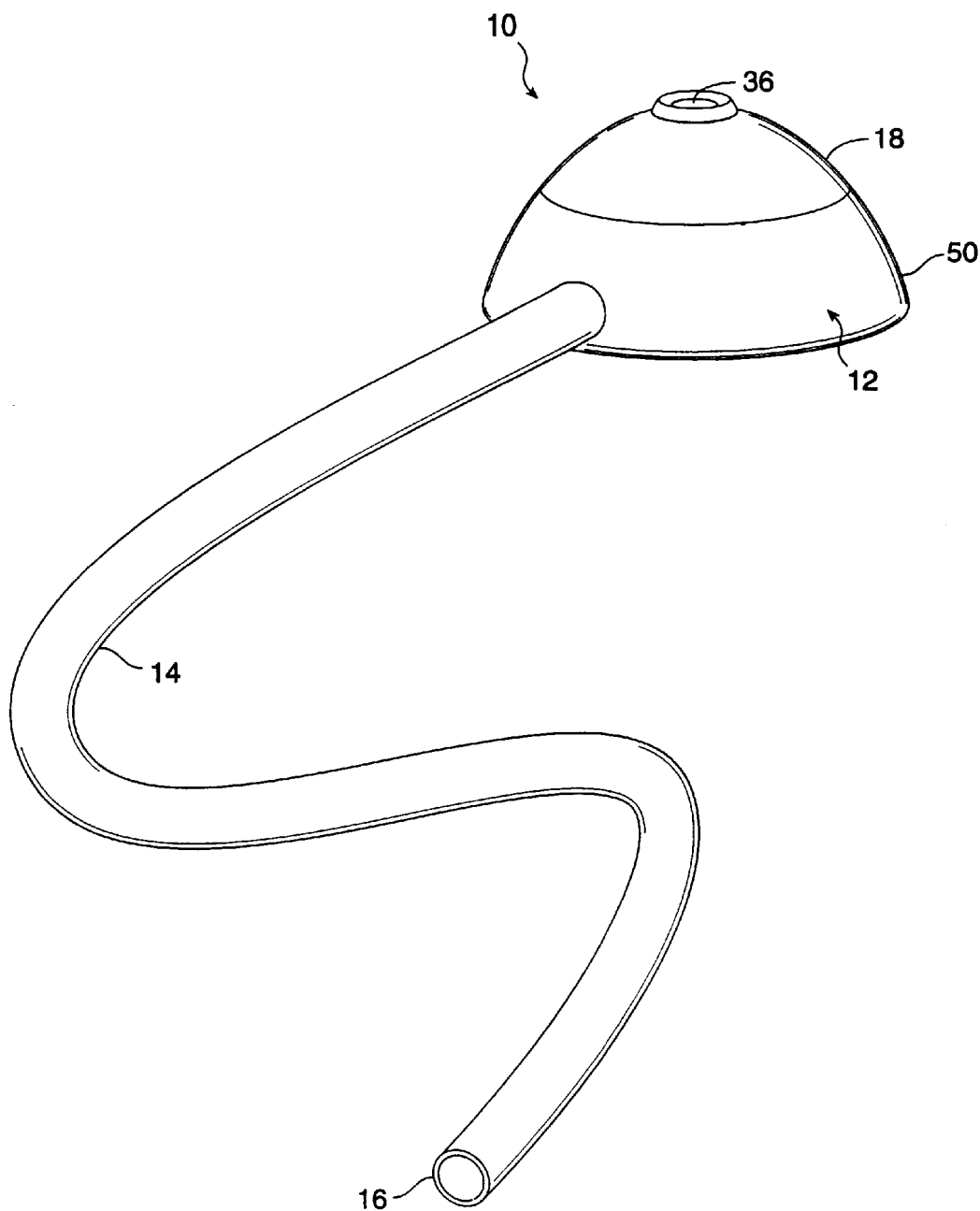
FIG. 1 is a perspective view of an access port having a flexible conduit extending therefrom constructed in accordance with the principles of the present invention.

The present invention provides methods and apparatus for facilitating percutaneous access to a body lumen of a patient. Exemplary body lumens, include blood vessels, the peritoneal cavity, and the like. The methods are particularly useful for accessing blood vessels, including both arterial blood vessels and venous blood vessels. While the remaining description is directed particularly at blood vessels, it will be appreciated that the invention applies to all body lumens and cavities where selective percutaneous access might be desired. For example, the ports can be used for introduction and removal of dialysate in peritoneal dialysis procedures. Access ports according to the present invention are implanted subcutaneously so that a passage therein lies a short distance beneath the surface of the patient's skin, typically being within 3 mm to 20 mm of the skin's surface. An access tube may then be percutaneously inserted into the passage in the access port in order to provide communication with the blood vessel or other body lumen via the access port. Such access can be provided for a variety of purposes, usually involving withdrawal of blood, the extracorporeal treatment of the withdrawn blood, and/or the return of the treated blood to the patient. Such extracorporeal blood treatment will most often be for hemodialysis, but can also be for hemofiltration, hemodiafiltration, apheresis, and the like. In addition to extracorporeal treatment, the access port of the present invention can be used for perfusing drugs, fluids, and other materials directly into a patient's circulation for a variety of purposes.

The present invention relies on implantation of the access port and connection of the port to the target blood vessel or other body lumen via a conduit, at least a portion of which will be flexible. By "flexible," it is meant that the conduit will be resilient and collapsible so that it may be externally clamped or otherwise deformed in order to prevent blood flow through the conduit when the access port is not in use. The use of external clamping in order to close the conduit is particularly advantageous since no internal structure need be provided within the conduit which could interfere with blood flow and/or with insertion of a needle or other access tube into the conduit.

The access tube will usually be a needle which can be directly pierced (percutaneously introduced) through the patient's skin and into the implanted port. Thus, the needle will usually have a sharpened tip in order to permit it to be self-introduced through the skin. Of course, access tubes having blunt distal ends could be used by first piercing the skin with a separate blade, stylet, needle, or the like, and thereafter introducing the access tube into the resulting incision or hole. The access tube could also be introduced using an internal stylet which is subsequently withdrawn, leaving the tube in place in the port. While the port of the present invention can accept a wide variety of different access tubes, it is significant that it can be used with standard hypodermic needles, standard fistula needles, large fistula needles, e.g. 16 gauge, 14 gauge, or larger, and the like. Prior port designs which employ a septum require the use of relatively small non-coring Huber needles or the use of a combination tube/stylet in order to avoid significant damage to the septum. The same is true of ports which employ slit valves through which a tube must pass, such as many of the Ensminger designs described above. In all cases, the needle or other access tube will be rigid and possess sufficient column strength in order to actuate a linkage for relieving clamping of the conduit, as described in more detail below.

The port of the present invention is also advantageous since it will not generally be damaged by use of an inappropriately sized needle or other access tube. While most prior art ports can be damaged through use of the wrong type or size of needle, the port of the present invention will not be damaged by larger needles (which simply engage the access aperture and do not pass into the port) or by smaller needles (which enter the access aperture but pass harmlessly into the interior of the base). In particular, the passage in the access port which receives the needle or other access tube will generally have at least one bend, usually a 90° elbow, which presents a surface which is engaged by a smaller needle. By forming or backing the passage from a material which is harder than the needle, e.g. a stainless steel, the port will be protected from any damage from improper insertion of a small needle.

An exemplary access port 10 comprising a base 12 and flexible conduit 14 is illustrated in FIGS. 1, 2, 2A, 3, and 3A. As shown in FIG. 1, the flexible conduit 14 extends from the base 12 and terminates at a distal end 16 which is suitable for direct anastomosis (suturing) to a blood vessel. Suitable conduit structures are described in U.S. Pat. No. 5,562,617, the full disclosure of which is incorporated herein by reference. Exemplary conduit structures may be composed of silicone rubber. Conduit structures having different distal ends are described with reference to FIGS. 4–8, hereinafter.

Figure 2:
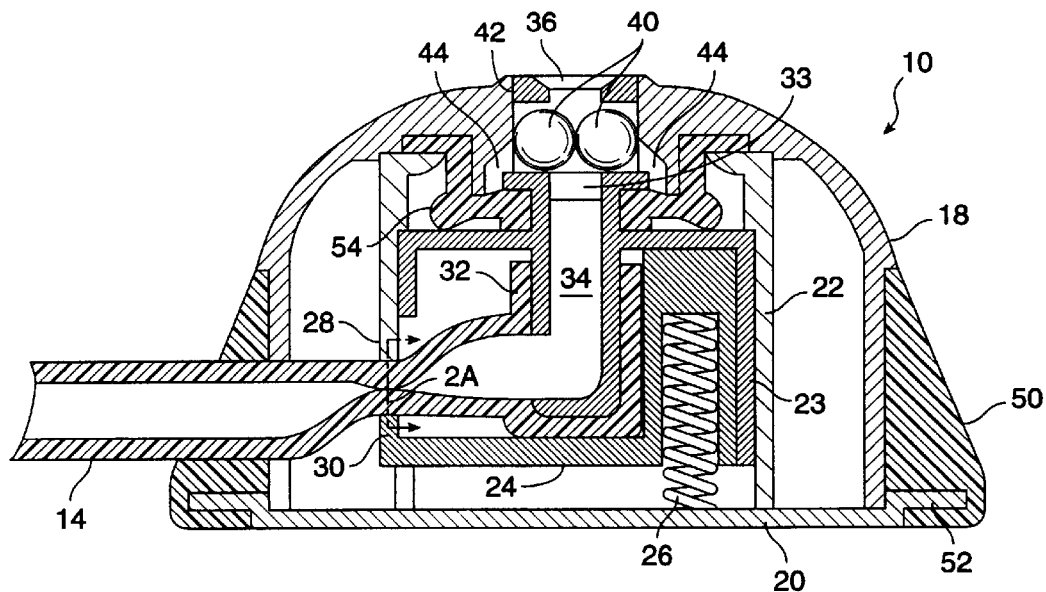
FIG. 2 is a side, cross-sectional view of the access port of FIG. 1 shown with a closed internal clamp structure.
Figure 2A:
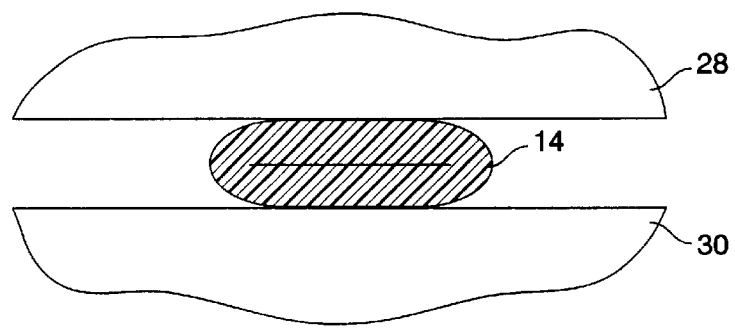
FIG. 2A is a partial cross-sectional view taken along line 2A—2A of FIG. 2.
Figure 3:
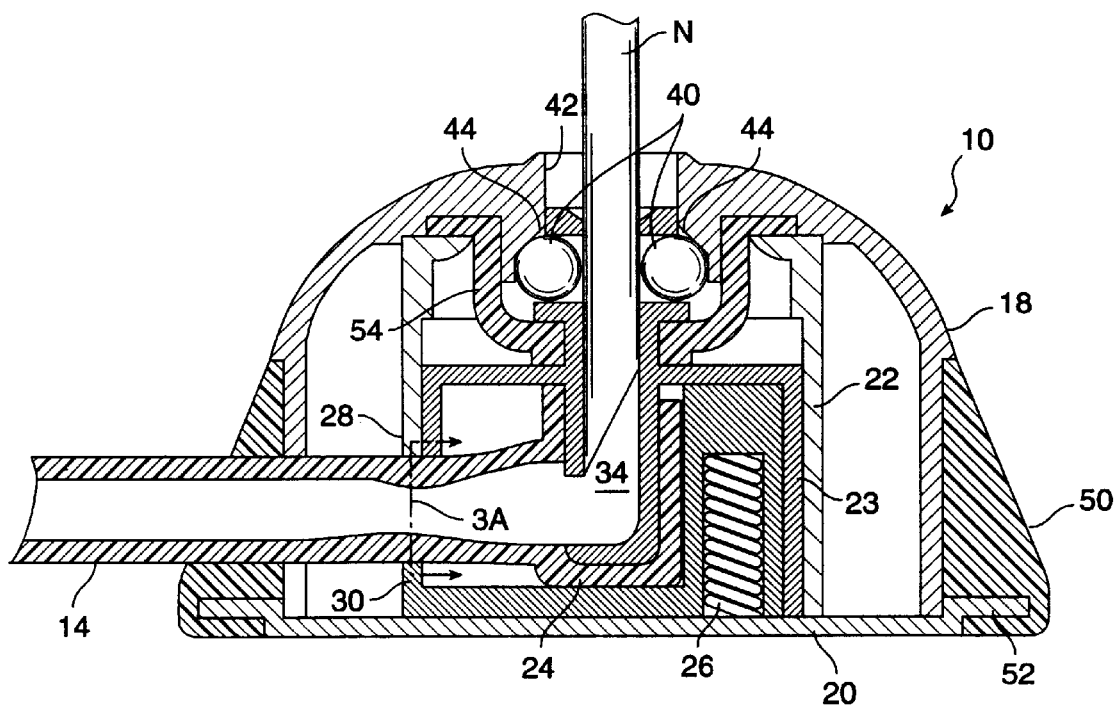
FIG. 3 is a side, cross-sectional view of the access port of FIG. 1 as shown with the internal clamp structure opened in response to the insertion of an access needle.
Figure 3A:
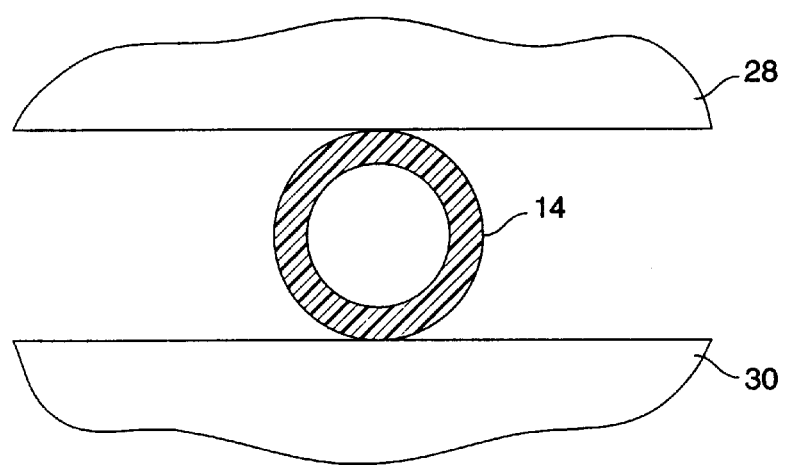
FIG. 3A is a partial cross-sectional view taken along line 3A—3A of FIG. 3.

The base 12 of access port 10 comprises an upper shell 18, a base plate 20, an internal cylinder 22, and a vertically reciprocating plunger 23 disposed within an actuator block 24, where the assembly of the plunger and actuator block are together disposed within the cylinder 22. As shown in FIGS. 2 and 2A, a spring 26 urges the plunger 23 and actuator block 24 upwardly relative to the base 20. When the plunger 23 and actuator block 24 are in their upward position, the conduit 14 is pinched closed between an upper lip 28 which is a portion of the wall of cylinder 22 and a lower lip 30 which is portion of the actuator block 24. A proximal end of the conduit 14 is connected to the lower end of a tube 32 which projects downwardly into an interior volume of the actuator block 24. The depending tube 32 provides an axial bore 34 for receiving a needle N, as illustrated in FIGS. 3 and 3A. A tapered region 33 is formed near the upper end of axial bore 34 and is sized to engage and seal against the outer side wall of a needle or other access tube which is introduced into the bore, as best seen in FIG. 3.

The needle N is introduced through an opening 36 at the upper end of the axial bore 34. Typically, though not necessarily, the opening 36 has a slight chamfer (conical shape) to facilitate alignment of the needle N as it is introduced into the bore 34. A pair of balls 40 are disposed in an upper portion of the tube 32 and contained within a circular aperture 42 in the shell 18 on the actuator block 24 as in its raised configuration, as shown in FIG. 2. When needle N is introduced through the opening 36, it will encounter the balls 40 and depress the plunger 23 and the actuator block 24 downward until the block reaches its lower configuration, as shown in FIG. 3. At that time, the balls 40 will move radially outward into an expanded portion 44 of the aperture 42. The balls 40 will thus become locked within the expanded region 44, holding the actuator block 24 in its lowered position, so long as the needle N remains in place.

When the actuator block 24 has been lowered, as shown FIGS. 3 and 3A, the opposed lips 28 and 30 are opened in order to relieve external clamping on the conduit 14. Thus, as the needle N is inserted into the access port 10, the clamping mechanism which has previously closed the flexible conduit 14 will be opened. When the needle N is removed, the spring 26 will urge the actuator block 24 upwardly, and the access port will return to the configuration shown in FIGS. 2 and 2A.

Conveniently, a silicone overmolding 50 is provided around the base of the access port 10 in order to facilitate implantation of the access port. A flange 52 extending radially outwardly from the base plate 20 will include holes (not illustrated) for suturing into tissue. The inclusion of the silicone overmolding 50 will prevent tissue ingrowth into the holes. Preferably, a silicone seal 54 will be provided between an internal surface of the upper shell 18 and an upper portion of the tube 32. The silicone seal 54 prevents the intrusion of blood or other fluids from surrounding tissue and/or which may leak from the needle N into the interior of the access port 10.

In a preferred aspect of the access port 10 of the present invention, the axial bore 34 will be tapered in the downward direction. The size of the bore and degree of the taper will be selected to frictionally engage conventional needles or other access tubes so that a tight seal is formed as the access tubes are inserted into the axial bore 34. The taper also provides a stop so that the needle N will not penetrate into the horizontal lumen defined by the conduit 14.

It can thus be seen that the combination of needle, access port 10, and flexible conduit 14 provides a substantially continuous and smooth flow path for fluids from and/or to the patient's vascular system. In particular, the use of external clamping for closing flow through the conduit 14 eliminates the need for an internal valve structure within the conduit or elsewhere within the access port to define a valve seat, i.e. that portion of the valve which closes to inhibit flow therethrough. The particular linkage shown for relieving clamping from the flexible conduit is simple, reliable, and relatively inexpensive to produce. Very few moving parts are needed, yet a positive seal is reliably achieved every time the needle N is withdrawn from the access port 10. Moreover, once the needle N is introduced into the access port 10, the clamp mechanism is locked in its open configuration to assure that full flow through the lumen of the flexible tube and other portions of the access port are maintained.

Figure 4:
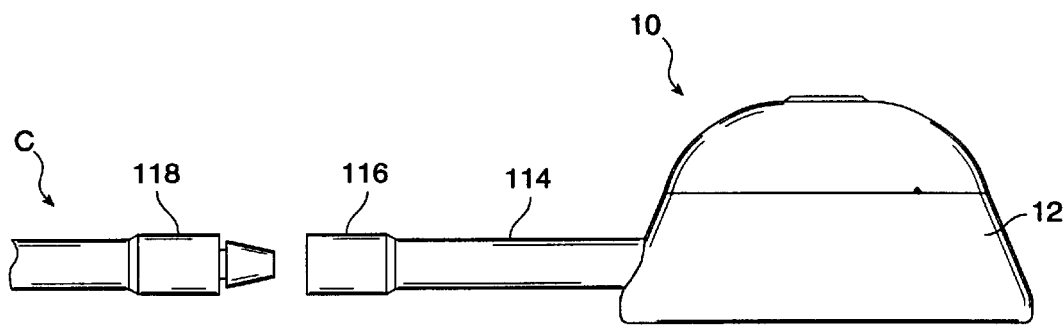
FIG. 4 illustrates an access port constructed in accordance with the principles of the present invention, wherein the flexible conduit is adapted for connection to a separate catheter.

Referring now to FIG. 4, the access port 10 may be modified to include a flexible conduit 114 having a distal fitting 116 for interconnection to a separate implantable catheter C. The fitting 116 will typically be a female fitting adapted to mate with a male fitting 118 at the proximal end of catheter C. Catheter C may be any known catheter intended for vascular attachment. For example, catheter C may be an indwelling catheter for venous attachment, or it may be adapted for direct attachment to an artery in any known fashion. Provision of a connector intermediate the port and the vasculature or body lumen has a number of benefits. The ability to implant the port separately from the catheter simplifies implantation. For example, it is possible to make two relatively small, separate incisions for implanting the port and attaching the catheter, respectively, and then to tunnel subcutaneously to permit interconnection. Such an approach reduces patient trauma. Replacement of the port and/or the catheter attachment is simplified since the two can be disconnected and one left undisturbed while the other is replaced. Such intermediate connections are preferably spaced relatively close to either the port or the lumenal connection, typically within 10 cm and often within 5 cm.

Figure 5:
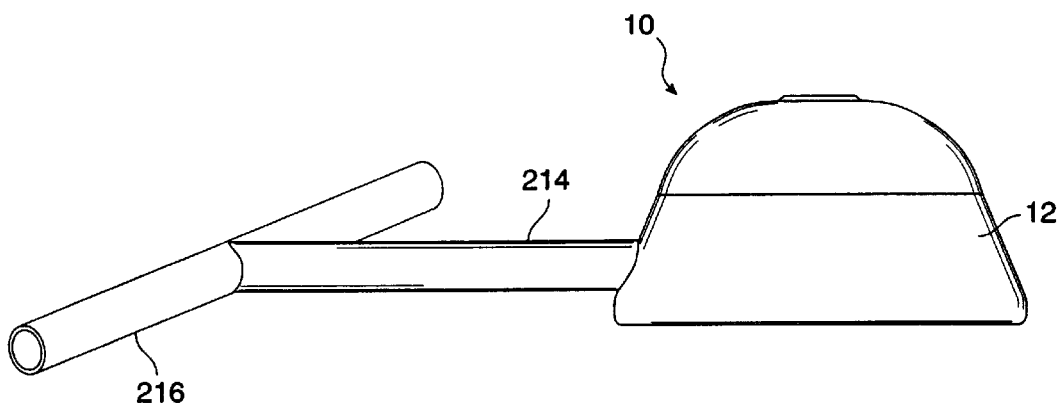
FIG. 5 illustrates an access port constructed in accordance with the principles of the present invention, wherein the distal end of the flexible conduit is adapted for direct insertion into the lumen of a blood vessel.

A further alternative structure for the access system 10 is illustrated in FIG. 5. There, flexible catheter 214 terminates in a T-connector 216. The T-connector is particularly suitable for implantation into arterial blood vessels, as described in co-pending application Ser. No. 08/724,948, the full disclosure of which is incorporated herein by reference.

Figure 6:
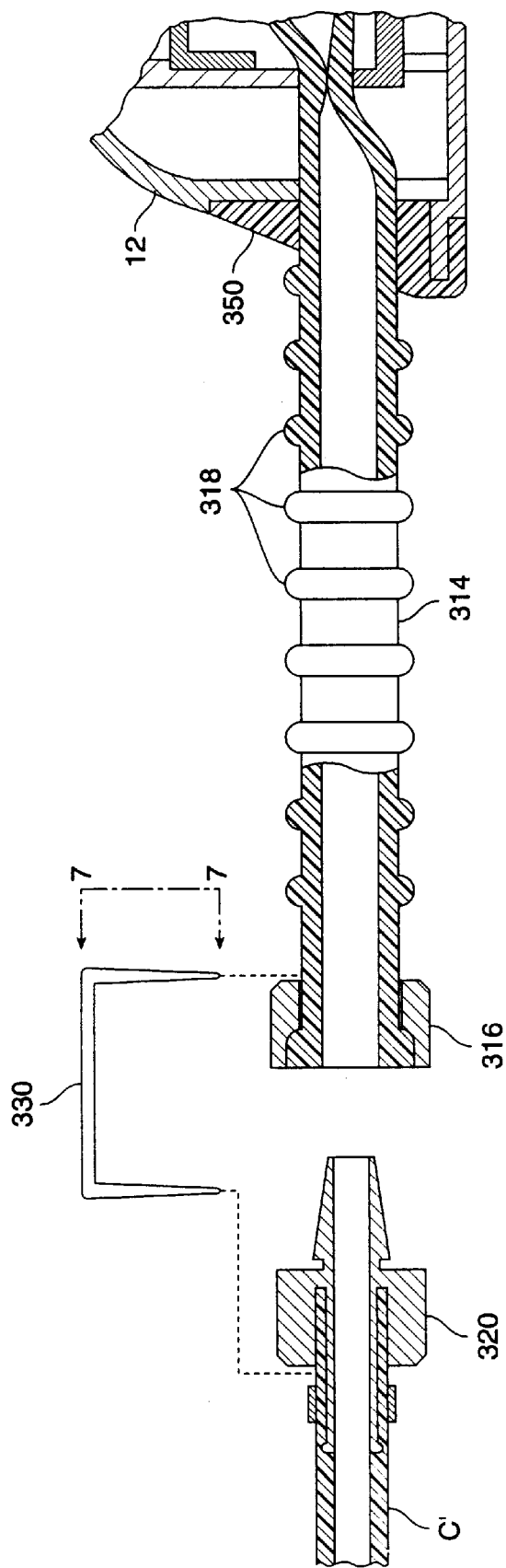
FIG. 6 is a partial, cross-sectional view of a specific flexible conduit having a distal connector for connection to the proximal end of an implantable catheter.
Figure 7:
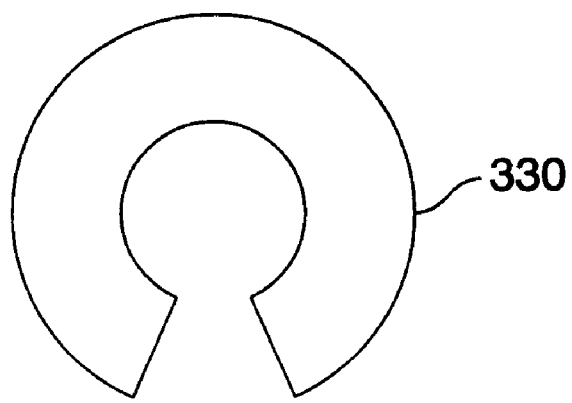
FIG. 7 is an end view taken along line 7—7 of FIG. 6.

Referring now to FIGS. 6 and 7, yet another alternative flexible conduit 314 which may be attached to base 12 of an access port 10 is illustrated. The flexible conduit 314 is formed integrally with the silicone overmolding 350, thus firmly anchoring the conduit to the base 12. While the internal portions of the conduit 314 are identical to those of conduit 14 and the earlier embodiments, the external portion of the conduit includes rib structures 318 in order to enhance hoop strength of the conduit. Moreover, a distal connector 316 is provided for connection to a male connector 320 at the proximal end of a catheter C', The connector 320 comprises a metal, usually titanium, fitting which is received within the lumen of the silicone conduit 314. A clip 330 is provided for securing over the connectors 316 and 320 after the port 312 and catheter C' have both been implanted and connected. The catheter connection mechanism shown in FIG. 6 is particularly advantageous since the catheter C' may be disconnected from the flexible conduit 314 without having to disturb the implantation of the base 12 of the access port.

Figure 8:
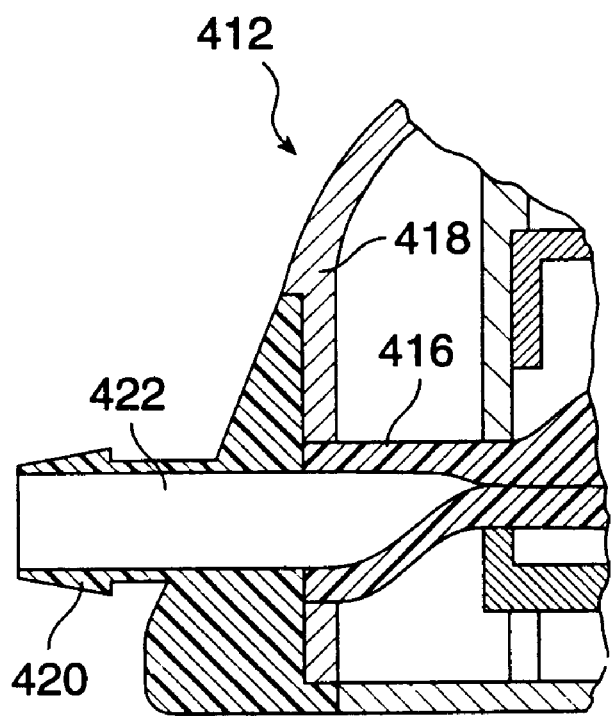
FIG. 8 illustrates an implantable access port similar to that of FIGS. 1–3, except that flexible conduit is terminated internally within the port and an external connector provided for connection to a separate, implantable catheter.

Referring now to FIG. 8, a base unit 412 is substantially similar to base unit 12 described previously, except that the flexible conduit 416 terminates at an aperture through the upper shell 418. A metal fitting 420 is provided to permit external connection of a catheter to the base unit 12. The fitting 420 defines a lumen 422 which is aligned with the lumen of the flexible conduit 416.

A presently preferred conduit connection where the internal pinch tube fits into a titanium nipple in the port housing is illustrated in FIG. 8. The conduit is attached externally to the titanium nipple and may terminate at its remote end (away from the housing) in any of the configurations previously discussed.

Figure 9A:
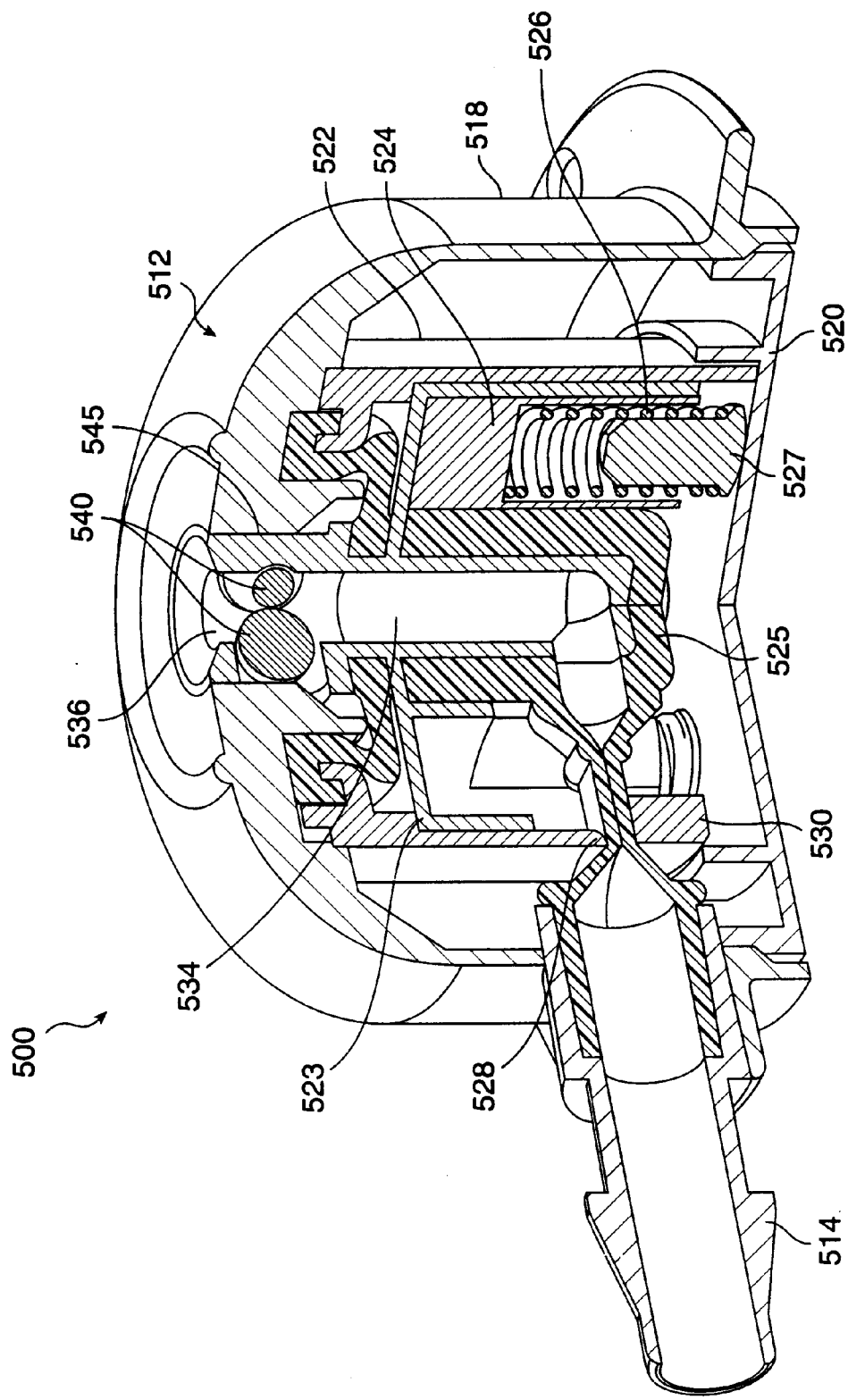
FIGS. 9A and 9B illustrate an alternative pinch tube connection design.
Figure 9B:
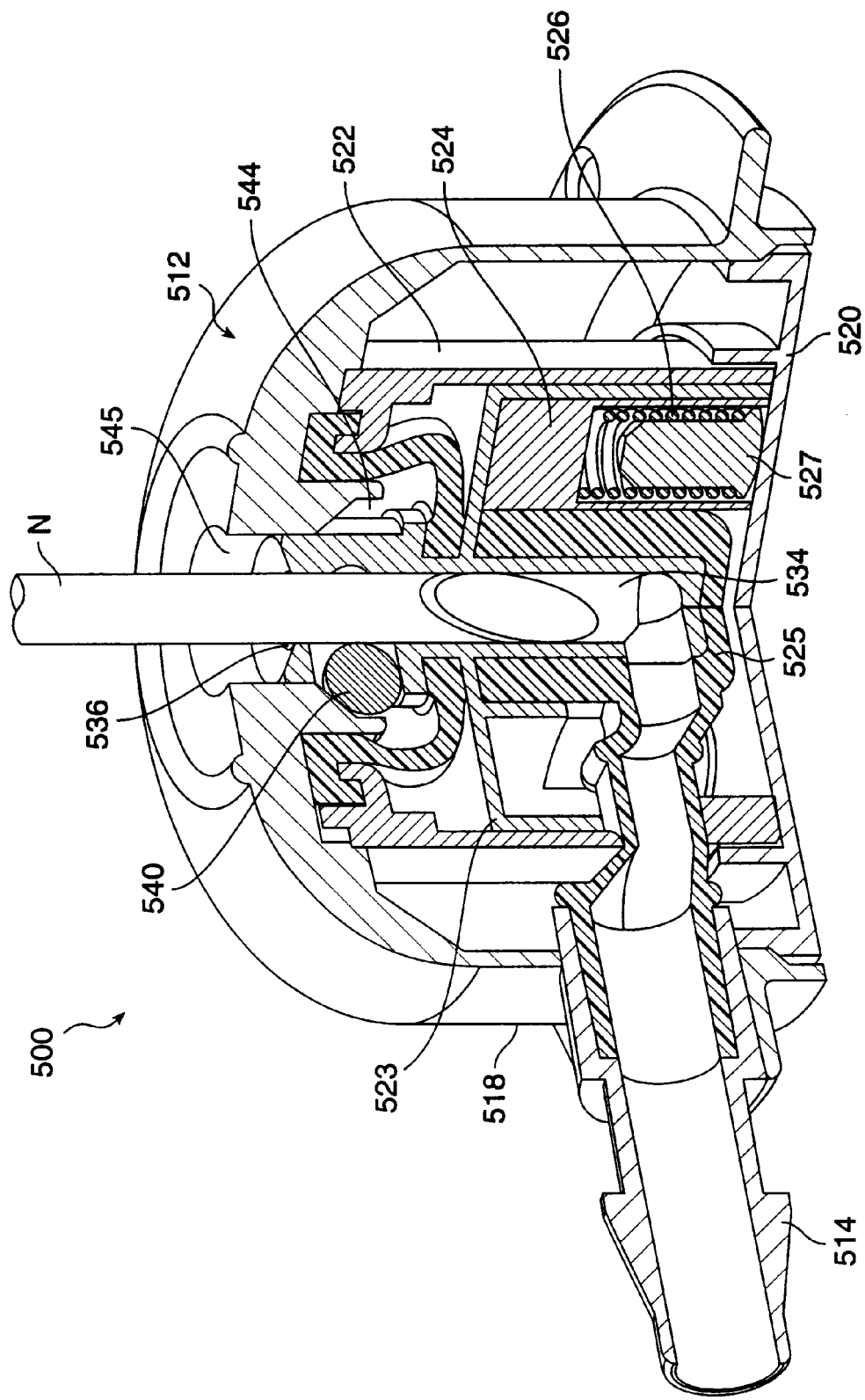

Referring now to FIGS. 9A and 9B, an additional embodiment of an access port 500 constructed in accordance with the principles of the present invention includes a body 512 having a nipple 514 extending laterally outward from the body 512. The nipple 514 is suitable for connection to a flexible conduit (not shown). The body 512 includes an upper shell 518, a base plate 520, an internal cylinder 522, a vertically reciprocating plunger 523 and an actuator block 524. The plunger 23/actuator block 524 are shown in their vertically raised position in FIG. 9A and their vertically depressed or lowered configuration in FIG. 9B.

Since the flexible conduit which connects to the nipple 514 does not extend into the base 512, the port embodiment 500 of FIGS. 9A and 9B employs a separate pinch tube 525, where the pinch tube is pinched closed between an upper lip 528 which is part of the cylinder 522 and a lower lip 530 which is part of the reciprocating actuator block 524. When the actuator block 524 is lowered, as shown in FIG. 9B, the external clamping of the pinch tube 525 is relieved.

The actuator block 524 is urged upwardly by spring 526 which is mounted over a pin 527, and the plunger 523 comprises an axial bore 534 for receiving a needle N, as shown in FIG. 9B. The needle N passes through aperture 536 and into the axial bore 534 in the plunger 523. As the needle enters the axial bore 534, it passes through opposed balls 540 which first cause lowering of the plunger 523 and the actuator block 524 and then are captured in an expanded portion 545 of the axial bore 534, as illustrated in FIG. 9B.

While the entry of needle N into the axial bore 534 and through opposed balls 540 may be effected simply by inserting the needle vertically downward, once the needle is fully lowered, and engaged by the tapered wall of axial bore 534 (as shown in FIG. 9B), the needle is "locked" in place by the balls 540. Surprisingly, it has been found that it is quite difficult to withdraw the needle from the balls 540, thus protecting the patient against accidental loss of the needle. Equally surprisingly, it has been found that simple twisting of the needle N about its axis allows the needle to be pulled from the port without significant hindrance. Thus, the combination of opposed balls 540 and the expanded region 545 for capturing the balls not only locks the valve open, it also secures the needle in place until it is desired to remove the needle.

Figure 10A:
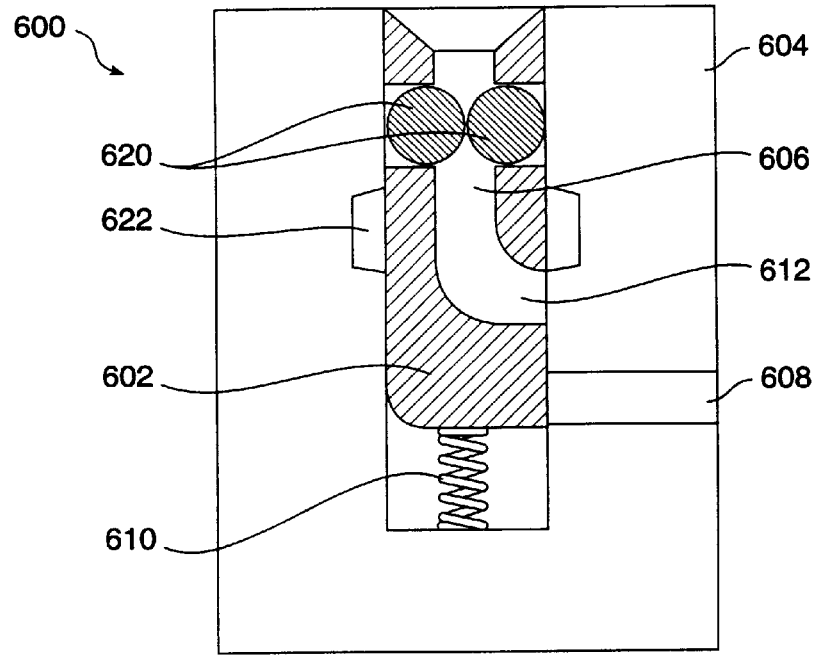
FIGS. 10A and 10B illustrate a slide valve embodiment of the implantable port of the present invention.
Figure 10B:
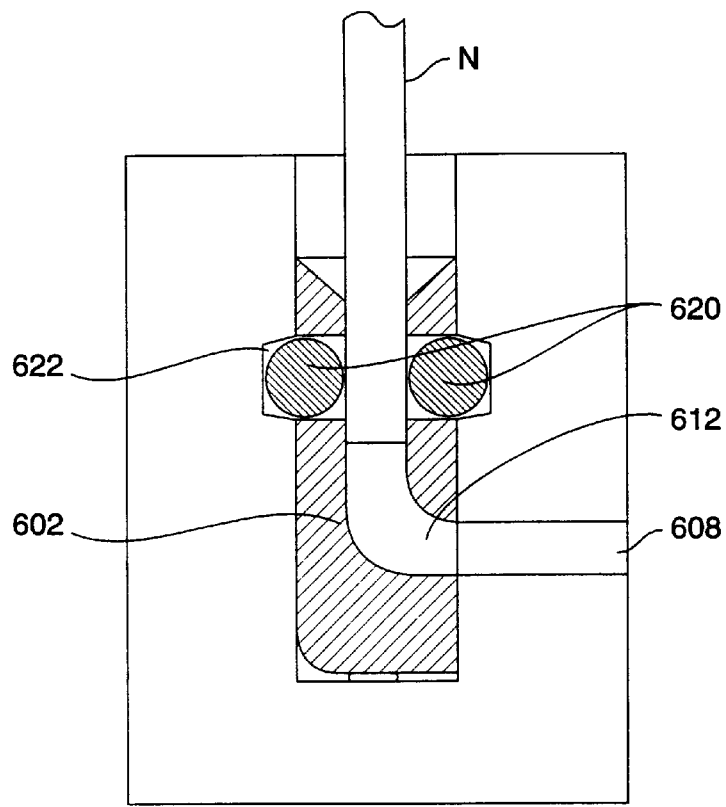

Referring now to FIGS. 10A and 10B, an alternative valve structure for use in the implantable ports of the present invention is illustrated. Instead of employing a pinch valve, as previously described, the ports may employ a sliding valve 600 where a reciprocating block 602 is formed within the base enclosure 604 (only a portion of which is illustrated). The reciprocating block 602 defines an inlet portion 606 of a passage through the port. An outlet portion 608 of the passage is also provided in the port. Initially, when no needle is present a spring 610 urges the reciprocating block 602 upward so that a side portion 612 of the passage is out of alignment with the outlet portion 608. Thus, the sliding valve structure 600 is closed. By introducing a needle N or other access tube into the valve structure 600, the reciprocating block 602 is lowered so that the side branch 612 of the passage comes into alignment with the outlet portion 608, as illustrated in FIG. 10B. The valve is thus open. The valve can be held in the open position by a pair of opposed balls 620 which are received in an enlarged recess 622, generally as described above in connection with the previous embodiments.

Although the foregoing invention has been described in some detail by way of illustration and example, for purposes of clarity of understanding, it will be obvious that certain changes and modifications may be practiced within the scope of the appended claims.

What is claimed is:

1. A method for percutaneously accessing a body lumen, said method comprising:
  maintaining a conduit between an implanted access port and the body lumen, said conduit being externally clamped; and
  percutaneously inserting an access tube into the access port, wherein the inserting step relieves the external clamping to permit fluid flow through the conduit.

2. A method as in claim 1, wherein the flow through the conduit is blood flow from the body lumen to the access port and access tube.

3. A method as in claim 2, wherein blood is withdrawn from the access port at a rate of at least 250 ml/min.

4. A method as in claim 3, wherein the blood flow rate is at least 300 ml/min.

5. A method as in claim 4, wherein the blood flow rate is at least 400 ml/min.

6. A method as in claim 5, wherein the blood flow rate is at least 500 ml/min.

7. A method as in claim 1, wherein the flow through the conduit is fluid flow from the access tube through the access port to the body lumen.

8. A method as in claim 7, wherein the fluid flow to the body lumen comprises blood flow.

9. A method as in claim 7, wherein the fluid flow to the body lumen comprises a drug.

10. A method as in claim 1, further comprising passing the blood through an external blood treatment circuit and returning the treated blood or a portion thereof to the patient.

11. A method as in claim 10, wherein the external blood treatment circuit comprises a hemodialysis circuit, a hemofiltration unit, or an apheresis circuit.

12. A method as in claim 1, wherein a proximal end of the conduit is disposed within the access port and a distal end of the conduit is attached to the body lumen.

13. A method as in claim 12, wherein the conduit comprises a single, continuous tube.

14. A method as in claim 12, wherein the conduit comprises at least two distinct axial portions.

15. A method as in claim 1, wherein a proximal end of the conduit is disposed within the access port and a distal end of the conduit terminates in a connector for attachment to a separate catheter.

16. A method as in claim 1, wherein a flexible portion of the conduit is clamped by a spring-loaded clamp mechanism and wherein insertion of the access tube actuates a linkage which overcomes the spring force to open the clamp mechanism.

17. A method as in claim 1, wherein the access tube is inserted in a direction generally normal to a patient's skin and wherein the conduit extends from the access port to the body lumen in a plane generally parallel to the patient's skin.

18. A method for percutaneously accessing a body lumen, said method comprising:
   maintaining a conduit between an implanted access port and the body lumen; and
   percutaneously inserting an access tube into the access port, wherein the access tube engages a linkage which opens a valve structure in the conduit which is located remotely from the portion of the access port into which the access tube has been inserted.

19. A method as in claim 18, wherein the flow through the conduit is blood flow from the body lumen to the access port and access tube.

20. A method as in claim 19, wherein blood is withdrawn from the access port at a rate of at least 250 ml/min.

21. A method as in claim 20, wherein the blood flow rate is at least 300 ml/min.

22. A method as in claim 21, wherein the blood flow rate is at least 400 ml/min.

23. A method as in claim 22, wherein the blood flow rate is at least 500 ml/min.

24. A method as in claim 18, wherein the flow through the conduit is fluid flow from the access tube through the access port to the body lumen.

25. A method as in claim 24, wherein the fluid flow to the body lumen comprises blood flow.

26. A method as in claim 24, wherein the fluid flow to the body lumen comprises a drug.

27. A method as in claim 18, wherein the valve structure comprises a spring-loaded clamp which constricts a flexible portion of the conduit when the linkage is not engaged by the access tube.

28. A method as in claim 18, wherein a proximal end of the conduit is disposed within the implantable port and a distal end of the conduit is attached to the body lumen.

29. A method as in claim 18, wherein the valve structure comprises a slide valve.

30. A method as in claim 18, wherein a reciprocatory block of the valve structure comprises the linkage which is actuated by the access tube, wherein actuation causes the block to move to align portions of the passage.

31. A method as in claim 30, wherein a proximal end of the conduit is disposed within the access port and a distal end of the conduit terminates in a connector for attachment to a separate catheter.

32. A method as in claim 18, further comprising passing the blood through an external blood treatment circuit and returning the treated blood or a portion thereof to the patient.

33. A method as in claim 18, wherein the external blood treatment circuit comprises a hemodialysis circuit, a hemofiltration unit, or an apheresis circuit.

34. A method for percutaneously accessing a body lumen, said method comprising:
   maintaining a conduit between an implanted access port and the body lumen; and
   percutaneously inserting an access tube into a tapered bore in a tube seat in the port to establish a generally fluid tight seal therewith;
   wherein insertion of the access tube actuates a linkage to open a valve disposed distally of the tube seat to permit flow to the conduit.

35. A method as in claim 34, wherein the flow through the conduit is blood flow from the body lumen to the access port and access tube.

36. A method as in claim 35, wherein blood is withdrawn from the access port at a rate of at least 250 ml/min.

37. A method as in claim 36, wherein the blood flow rate is at least 300 ml/min.

38. A method as in claim 37, wherein the blood flow rate is at least 400 ml/min.

39. A method as in claim 38, wherein the blood flow rate is at least 500 ml/min.

40. A method as in claim 34, wherein insertion of the access tube into the tube seat depresses the tube seat relative to the base which in turn actuates the linkage.

41. A method as in claim 40, wherein the tube seat is locked in the depressed condition until the access tube is removed.

42. A method as in claim 34, wherein a proximal end of the conduit is disposed within the access port and a distal end of the conduit is attached to the body lumen.

43. A method as in claim 42, wherein conduit comprises a single, continuous tube.

44. A method as in claim 42, wherein the conduit comprises at least two distinct axial portions.

45. A method as in claim 34, wherein the flow through the conduit is fluid flow from the access tube through the access port to the body lumen.

46. A method as in claim 45, wherein the fluid flow to the body lumen comprises blood flow.

47. A method as in claim 45, wherein the fluid flow to the body lumen comprises a drug.

48. A method as in claim 34, wherein the tube seat comprises a tapered bore which frictionally engages the outside of the access tube as the tube is inserted into the bore.

49. A method as in claim 34, wherein a proximal end of the conduit is disposed within the access port and a distal end of the conduit terminates in a connector for attachment to a separate catheter.

50. A method as in claim 34, further comprising passing the blood through an external blood treatment circuit and returning the treated blood or a portion thereof to the patient.

51. A method as in claim 34, wherein the external blood treatment circuit comprises a hemodialysis circuit, a hemofiltration unit, or an apheresis circuit.

52. A method for percutaneously accessing a body lumen, said method comprising:

maintaining a conduit between an implanted access port and the body lumen; and percutaneously inserting a rigid access tube into a cylindrical passage in the access port in a vertical orientation, wherein the passage is connected to the conduit through an elbow of from 75° to 105°.

53. A method as in claim 52, wherein the flow through the conduit is blood flow from the body lumen to the access port and access tube.

54. A method as in claim 53, wherein blood is withdrawn from the access port at a rate of at least 250 ml/min.

55. A method as in claim 54, wherein the blood flow rate is at least 300 ml/min.

56. A method as in claim 55, wherein the blood flow rate is at least 400 ml/min.

57. A method as in claim 56, wherein the blood flow rate is at least 500 ml/min.

58. A method as in claim 53, wherein the fluid flow to the body lumen comprises blood flow.

59. A method as in claim 52, wherein the conduit is externally clamped and wherein the inserting step relieves the external clamping to permit fluid flow through the conduit.

60. A method as in claim 59, wherein a flexible portion of the conduit is clamped by a spring-loaded clamp mechanism and wherein insertion of the access tube actuates a linkage which overcomes the spring force to open the clamp mechanism.

61. A method as in claim 60, wherein the access tube is inserted in a direction generally normal to a patient's skin and wherein the conduit extends from the access port to the body lumen in a plane generally parallel to the patient's skin.

62. A method as in claim 52, wherein a proximal end of the conduit is disposed within the access port and a distal end of the conduit is attached to the body lumen.

63. A method as in claim 62, wherein conduit comprises a single, continuous tube.

64. A method as in claim 62, wherein the conduit comprises a composite structure having at least two distinct axial portions.

65. A method as in claim 52, wherein a proximal end of the conduit is disposed within the access port and a distal end of the conduit terminates in a connector for attachment to a separate catheter.

66. A method as in claim 53, wherein the flow through the conduit is fluid flow from the access tube through the access port to the body lumen.

67. A method as in claim 52, wherein the fluid flow to the body lumen comprises a drug.

68. A method as in claim 52, further comprising passing the blood through an external blood treatment circuit and returning the treated blood or a portion thereof to the patient.

69. A method as in claim 52, wherein the external blood treatment circuit comprises a hemodialysis circuit, a hemofiltration unit, or an apheresis circuit.

70. An implantable port comprising:

a base having a passage with (a) an inlet for receiving an access tube and (b) an outlet;

a linkage actuated by insertion of an access tube into the inlet; and a valve structure which opens the passage downstream from the inlet in response to actuation of the linkage by an access tube.

71. An implantable port as in claim 70, wherein the valve structure comprises a flexible conduit and a clamp which opens and closes about the conduit in response to actuation of the linkage.

72. An implantable port as in claim 71, wherein the passage comprises a tapered bore which seals against the access tube as said tube is inserted therein.

73. An implantable port as in claim 72, wherein the flexible conduit is attached to a small diameter end of the tapered bore.

74. An implantable port as in claim 73, wherein the flexible conduit is attached to the tapered bore at an angle from 75° to 105°.

75. An implantable port as in claim 74, wherein the flexible conduit has a proximal end disposed within the base and a distal end which terminates on a connector on an external surface of the base.

76. An implantable port as in claim 71, wherein the flexible conduit has a proximal end disposed within the base and a distal end disposed outside of the base.

77. An implantable port as in claim 76, wherein the distal end of the conduit is adapted for direct connection to a body lumen.

78. An implantable port as in claim 76, wherein the distal end of the conduit is adapted for connection to one end of a catheter.

79. An implantable port as in claim 76, wherein the distal end of the conduit terminates in a lower connector.

80. An implantable port as in claim 71, wherein the passage and the conduit are joined to form a substantially continuous flow lumen which is free from stagnant regions.

81. An implantable port as in claim 71, wherein the flexible conduit has a proximal end disposed within the base and a distal end which terminates on a connector on an external surface of the base.

82. An implantable port as in claim 71, wherein the linkage assembly is disposed wholly within the base.

83. An implantable port as in claim 71, wherein the linkage is actuated by passage of the access tube into the passage which results in release of a clamp from the exterior of the flexible conduit.

84. An implantable port as in claim 70, wherein the valve structure comprises a slide valve.

85. An implantable port as in claim 84, wherein the slide valve comprises a reciprocating block having the inlet portion of the passage formed therein, wherein the reciprocating block comprises the linkage.

86. An implantable port as in claim 85, wherein insertion of an access tube in the reciprocating block slides the block so that the passage therein becomes aligned with a downstream portion of the passage in the base.

87. An implantable port comprising:

a base having a passage for receiving an access tube;

a flexible conduit disposed to establish fluid flow with an access tube inserted through the passage; and a clamp disposed externally about the flexible conduit, wherein the clamp opens about the conduit to permit fluid flow therethrough when an access tube is inserted into the passage and closes over the conduit when the access tube is removed from the passage.

88. An implantable port as in claim 87, wherein the passage comprises a tapered bore which seals against the access tube as said tube is inserted therein.

89. An implantable port as in claim 88, wherein the flexible conduit is attached to a small diameter end of the tapered bore.

90. An implantable port as in claim 89, wherein the flexible conduit is attached to the tapered bore at an angle from 75° to 105°.

91. An implantable port as in claim 87, further comprising a linkage assembly including an actuator which senses entry of the access tube into the passage in the base and which opens the clamp in response to such passage.

92. An implantable port as in claim 91, wherein the linkage assembly is disposed wholly within the base.

93. An implantable port as in claim 87, wherein the flexible conduit has a proximal end disposed within the base and a distal end disposed outside of the base.

94. An implantable port as in claim 93, wherein the passage and the conduit are joined to form a substantially continuous flow lumen which is free from stagnant regions.

95. An implantable port as in claim 93, wherein the distal end of the conduit is adapted for direct connection to a body lumen.

96. An implantable port as in claim 93, wherein the distal end of the conduit is adapted for connection to one end of a catheter.

97. An implantable port as in claim 93, wherein the distal end of the conduit terminates in a lower connector.

98. An implantable port comprising:
a base having a cylindrical inlet passage for receiving an access tube, and an outlet passage disposed to receive fluid flow from an access tube inserted through the inlet passage;
wherein the inlet passage is oriented along a vertical axis and the outlet passage is disposed along a horizontal axis.

99. An implantable port as in claim 98, wherein the inlet passage and the outlet passage are joined to form a substantially continuous flow lumen which is free from stagnant regions.

100. An implantable port as in claim 99, wherein the outlet passage comprises a flexible catheter and the vertically oriented inlet passage is defined by a rigid tube.

101. An implantable port as in claim 100, wherein the inlet passage comprises a tapered bore which seals against the access tube as said tube is inserted therein.

102. An implantable port as in claim 101, wherein the flexible conduit is attached to a small diameter end of the tapered bore.

103. An implantable port as in claim 102, wherein the flexible conduit is attached to the tapered bore at an angle from 75° to 105°.

104. An implantable port as in claim 100, wherein the flexible catheter is joined to the rigid tube at an elbow having an angle from 75° to 105°.

105. An implantable port as in claim 98, wherein the outlet passage comprises a proximal end disposed within the base and a distal end disposed outside of the base.

106. An implantable port as in claim 105, wherein the distal end of the flexible conduit of the outlet passage is adapted for direct connection to a body lumen.

107. An implantable port as in claim 105, wherein the distal end of the conduit is adapted for connection to one end of a catheter.

108. An implantable port as in claim 105, wherein the distal end of the conduit terminates in a connector external to the base.

109. An implantable port as in claim 98, further comprising a linkage assembly and a valve, said linkage assembly being actuated by entry of the access tube into the inlet which entry opens the valve.

110. An implantable port as in claim 109, wherein entry of the access tube moves the linkage assembly in the direction of the access tube.

111. An implantable port as in claim 98, wherein the flexible conduit has a proximal end disposed within the base and a distal end which terminates on a connector on an external surface of the base.

112. An implantable port comprising:
a base having a first passage for receiving an access tube;
a flexible conduit disposed through a second passage in the base;
an actuator assembly reciprocatably received in the base having a bore aligned with the first passage for receiving the access tube, wherein a proximal end of the flexible conduit is mechanically coupled to the bore in the actuator assembly; and
a spring for urging the actuator assembly to a first position in the base wherein the relative position of the actuator assembly and the second passage closes the flexible conduit and wherein insertion of the access tube into the first passage shifts the actuator assembly to a second position which opens the flexible conduit.

113. An implantable port as in claim 112, wherein the bore comprises a tapered bore which seals against an access tube as said tube is inserted therein.

114. An implantable port as in claim 113, wherein the flexible conduit is attached to a small diameter end of the tapered bore.

115. An implantable port as in claim 114, wherein the flexible conduit is attached to the tapered bore at an angle from 75° to 105°.

116. An implantable port as in claim 112, wherein the actuator assembly comprises a lower lip and the second passage in the base comprises an upper lip, wherein the upper an lower lips are opposed on opposite sides or the flexible conduit so that the spring closes said lips together to close the lumen within the conduit.

117. An implantable port as in claim 112, wherein the flexible conduit has a proximal end disposed within the base and a distal end disposed outside of the base.

118. An implantable port as in claim 112, wherein the distal end is adapted for direct connection to a body lumen.

119. An implantable port as in claim 112, wherein the distal end of the conduit is adapted for connection to one end of a catheter.

120. An implantable port as in claim 112, wherein the distal end of the conduit teminates in a lower connector.

121. An implantable port as in claim 112, wherein the flexible conduit has proximal end disposed within the base and a distal end which terminates on a connector on an external surface of the base.

122. An implantable port as in claim 112, wherein the actuator assembly and spring are disposed wholly within the base.

123. An implantable port comprising:

a base having a passage for receiving an access tube;

a valve assembly in the base, said valve assembly having a bore which is aligned with the passage and receives the access tube;

a pair of balls disposed between the passage in the base and the bore in the valve, wherein the balls are spring-biased to close against and lock the access tube when the access tube is inserted through the passage and port.

124. An implantable port as in claim 123, wherein the valve comprises an assembly that is reciprocatably mounted within the base and a spring which urges the assembly toward the passage in the base, wherein the balls are disposed over the assembly and move radially outwardly into an expanded region of the passage as they move downward in response to insertion of the access tube.

* * * * *